United States Patent
Spoerker

(10) Patent No.: US 11,262,282 B2
(45) Date of Patent: *Mar. 1, 2022

(54) ANALYZING DRILLING FLUID RHEOLOGY AT A DRILLING SITE

(71) Applicant: Saudi Arabian Oil Company, Dhahran (SA)

(72) Inventor: Hermann F. Spoerker, Dhahran (SA)

(73) Assignee: Saudi Arabian Oil Company, Dhahran (SA)

(*) Notice: Subject to any disclaimer, the term of this patent is extended or adjusted under 35 U.S.C. 154(b) by 205 days.

This patent is subject to a terminal disclaimer.

(21) Appl. No.: 16/696,539

(22) Filed: Nov. 26, 2019

(65) Prior Publication Data
US 2020/0096428 A1    Mar. 26, 2020

Related U.S. Application Data

(63) Continuation of application No. 15/157,635, filed on May 18, 2016, now Pat. No. 10,564,083.

(51) Int. Cl.
*G01N 11/04* (2006.01)
*E21B 41/00* (2006.01)
(Continued)

(52) U.S. Cl.
CPC .............. *G01N 11/04* (2013.01); *E21B 21/01* (2013.01); *E21B 21/06* (2013.01); *E21B 41/00* (2013.01);
(Continued)

(58) Field of Classification Search
CPC .... G01N 11/04; G01N 11/08; G01N 33/2823; G06F 30/20; E21B 21/01; E21B 41/00; E21B 49/005; G01V 99/005
See application file for complete search history.

(56) References Cited

U.S. PATENT DOCUMENTS 1,945,822 A    2/1934  Nivling
2,960,861 A    11/1960 Copland et al.
(Continued)

FOREIGN PATENT DOCUMENTS

AU           449045           5/1974
WO       2015/168689         11/2015
(Continued)

OTHER PUBLICATIONS

Vajargah, Ali Karimi, and Eric van Oort. "Determination of drilling fluid rheology under downhole conditions by using real-time distributed pressure data." Journal of natural gas science and engineering 24 (2015): 400-411. (Year: 2015).*
(Continued)

*Primary Examiner* — Chuen-Meei Gan
(74) *Attorney, Agent, or Firm* — Fish & Richardson P.C.

(57) ABSTRACT

The present disclosure describes methods and systems for analyzing drilling fluid rheology at a drilling site. One method includes obtaining, from a wellbore drilling system implementing a wellbore drilling operation at a wellbore drilling site, a sample of a drilling fluid being used in the wellbore drilling operation at the wellbore drilling site; flowing the sample through an elongated tubular member at a plurality of different flow rates, the elongated tubular member installed at the wellbore drilling site; measuring, at the wellbore drilling site and at each flow rate, a stress-strain response of the sample in response to each flow rate; generating a plurality of stress-strain responses for the sample at the corresponding plurality of different flow rates, the plurality of stress-strain responses including each stress-strain response of the sample measured at each flow rate; and returning the sample to the wellbore drilling operation.

16 Claims, 6 Drawing Sheets

(51) Int. Cl.
*E21B 21/06* (2006.01)
*G01N 11/08* (2006.01)
*E21B 49/00* (2006.01)
*G01N 33/28* (2006.01)
*G06F 30/20* (2020.01)
*E21B 21/01* (2006.01)
*G01V 99/00* (2009.01)

(52) U.S. Cl.
CPC ............ *E21B 49/005* (2013.01); *G01N 11/08* (2013.01); *G01N 33/2823* (2013.01); *G01V 99/005* (2013.01); *G06F 30/20* (2020.01)

(56) References Cited

U.S. PATENT DOCUMENTS

| | | | |
|---|---|---|---|
| 2,987,923 | A | 6/1961 | Hoeppel et al. |
| 3,468,158 | A | 9/1969 | Chien |
| 4,352,287 | A | 10/1982 | Orth |
| 4,557,142 | A | 12/1985 | Hensley et al. |
| 4,821,564 | A | 4/1989 | Pearson et al. |
| 7,584,165 | B2 | 9/2009 | Buchan |
| 7,832,257 | B2 | 11/2010 | Weightman et al. |
| 8,881,577 | B1 | 11/2014 | Agar et al. |
| 9,097,103 | B2 | 8/2015 | Pop |
| 9,134,291 | B2 | 9/2015 | Jamison et al. |
| 2008/0289875 | A1* | 11/2008 | Burge ............... G06F 30/13 175/40 |
| 2013/0025359 | A1 | 1/2013 | Cartellieri |
| 2014/0262516 | A1* | 9/2014 | Larson ............... G01N 33/2823 175/48 |
| 2015/0059446 | A1 | 3/2015 | Agar et al. |
| 2018/0356325 | A1* | 12/2018 | Cho ..................... G01N 13/02 |

FOREIGN PATENT DOCUMENTS

| | | |
|---|---|---|
| WO | 2015/191091 | 12/2015 |
| WO | 2016/054628 | 4/2016 |

OTHER PUBLICATIONS

International Search Report and Written Opinion of the International Searching Authority issued in International Application No. PCT/US2017/023766 dated Jul. 13, 2017; 16 pages.

Gulf Cooperation Council Examination Report issued in GCC Application No. GC 2017-33213 dated Jan. 5, 2019, 5 pages.

Gulf Cooperation Council Examination Report issued in GCC Application No. GC 2017-33213 dated Apr. 21, 2019, 4 pages.

World Oil, Composite Catalog of Oil Field Equipment and Services, "Well Servicing Equipment—BJ Mud Density Control System," published in 1980-1981, 3 pages.

Adesina et al., "SPE 167551 Investigating the Carrying Capacity and the Effect of Drilling Cutting on Rheological Properties of Jatropha Oil Based Mud 1"; SPE Nigeria Annual International Conference and Exhibition; Lagos, Nigeria; Aug. 5-7, 2013; 8 pages.

Vajargah and Oort, "Determination of drilling fluid rheology under downhole conditions by using real-time distributed pressure data," Journal of Natural Gas Science and Engineering, vol. 24, Apr. 12, 2015.

* cited by examiner

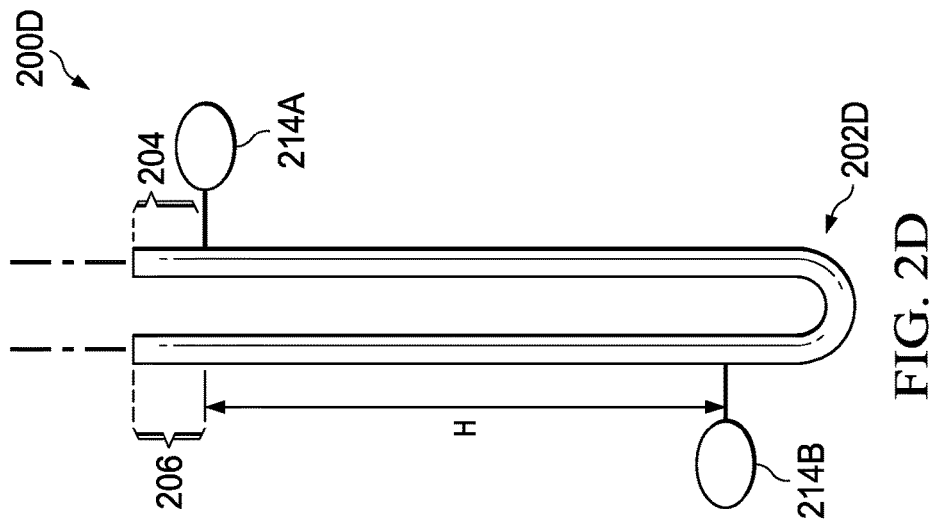
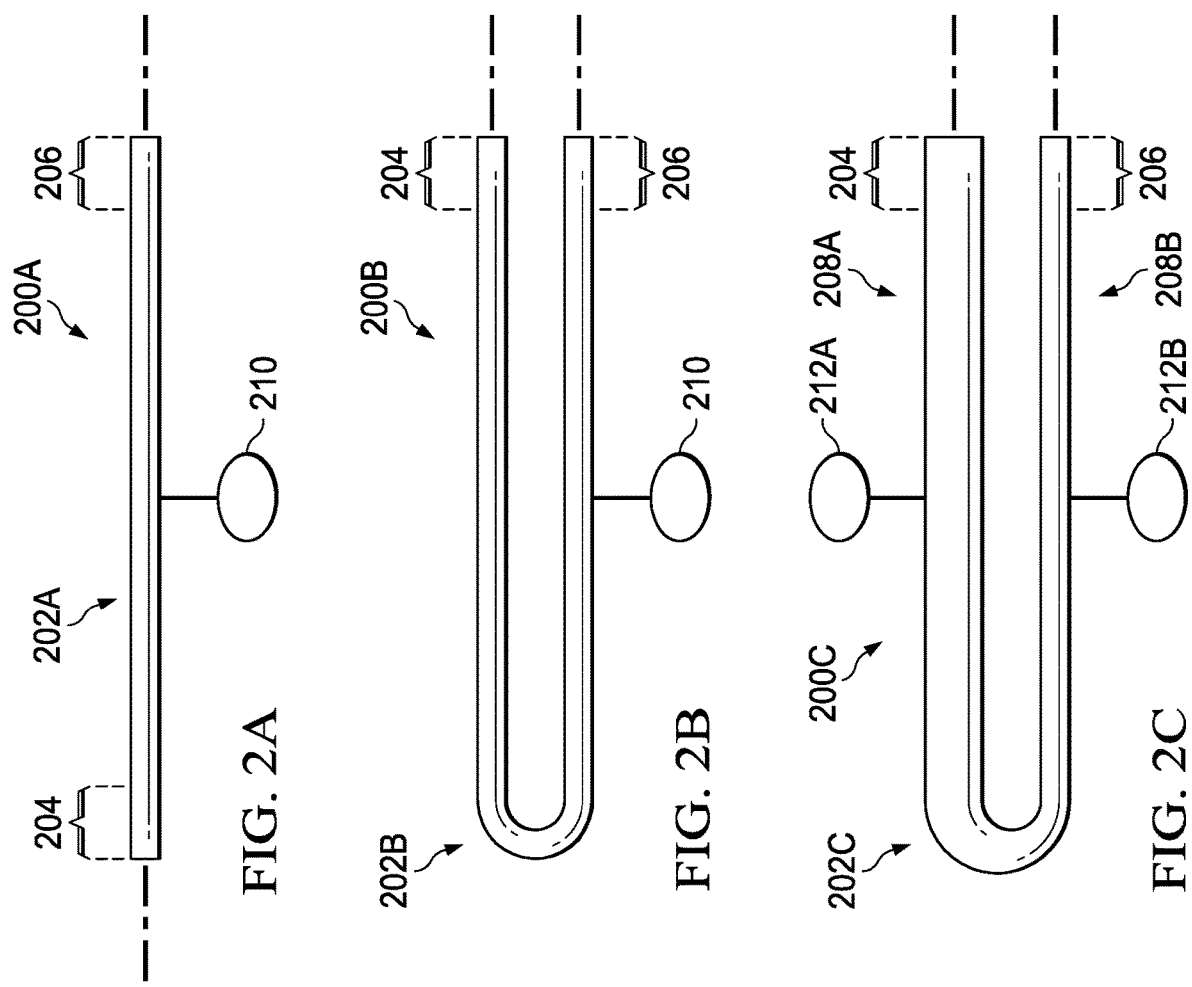

ANALYZING DRILLING FLUID RHEOLOGY AT A DRILLING SITE

CROSS-REFERENCE TO RELATED PATENT APPLICATIONS

This application is a continuation of and claims the benefit of priority to U.S. patent application Ser. No. 15/157,635, filed May 18, 2016, the contents of which are incorporated by reference herein.

TECHNICAL FIELD

This specification relates to analyzing drilling fluid rheology.

BACKGROUND

In wellbore drilling operations, a drilling fluid is flowed from a surface through a drill string and into a drill bit drilling the formation. The drilling fluid flows through the drill bit and returns to the surface through an annulus formed between the side walls of the wellbore and the drill string. Rheological properties of the drilling fluid affect the effectiveness of the wellbore drilling operation. For example, a change in viscosity of the drilling fluid can be an indication that certain additives to the drilling fluid have been lost to the formation and need to be replenished.

SUMMARY

This specification describes technologies relating to analyzing drilling fluid rheology at a drilling site. In general, one innovative aspect of the subject matter described in this specification can be embodied in methods that include the actions of obtaining, from a wellbore drilling system implementing a wellbore drilling operation at a wellbore drilling site, a sample of a drilling fluid being used in the wellbore drilling operation at the wellbore drilling site; flowing the sample through an elongated tubular member at a plurality of different flow rates, the elongated tubular member installed at the wellbore drilling site; measuring, at the wellbore drilling site and at each flow rate, a stress-strain response of the sample in response to each flow rate; generating a plurality of stress-strain responses for the sample at the corresponding plurality of different flow rates, the plurality of stress-strain responses including each stress-strain response of the sample measured at each flow rate; and returning the sample to the wellbore drilling operation.

The foregoing and other implementations can each, optionally, include one or more of the following features, alone or in combination:

A first aspect, combinable with the general implementation, wherein the sample is an on-site sample, the plurality of stress-strain responses is a plurality of on-site stress-strain responses, and wherein the method further comprises: obtaining, from the wellbore drilling system, a laboratory sample of the drilling fluid; measuring, in a laboratory and at each flow rate, a laboratory stress-strain response of the laboratory sample in response to each flow rate; generating a plurality of laboratory stress-strain responses for the laboratory sample at the corresponding plurality of different flow rates, the plurality of laboratory stress-strain responses including each laboratory stress-strain response of the laboratory sample measured at each flow rate; comparing the plurality of laboratory stress-strain responses to the plurality of on-site stress-strain responses; and adjusting a mathematical model representing stress-strain behavior of the drilling fluid based on a result of comparing the plurality of laboratory stress-strain responses to the plurality of on-site stress-strain responses.

A second aspect, combinable with any of the previous aspects, wherein the method further comprises providing the plurality of stress-strain responses for the sample as an input to a computer application configured to simulate the wellbore drilling operation; and simulating a performance of the drilling fluid in the wellbore drilling operation using the plurality of stress-strain responses as an input.

A third aspect, combinable with any of the previous aspects, wherein simulating the performance of the drilling fluid in the wellbore drilling operation comprises simulating at least one of a friction pressure of the drilling fluid or cutting carrying capacity of the drilling fluid in the wellbore drilling operation.

A fourth aspect, combinable with any of the previous aspects, wherein the wellbore drilling operation comprises a drilling fluid holding tank configured to receive the drilling fluid being used in the wellbore drilling operation, and wherein obtaining the sample of the drilling fluid comprises: connecting the drilling fluid holding tank to the elongated tubular member; and flowing the sample from the drilling fluid holding tank to the elongated tubular member.

A fifth aspect, combinable with any of the previous aspects, wherein the method further comprises installing the elongated tubular member in a horizontal orientation, and wherein measuring, at the wellbore drilling site and at each flow rate, a stress-strain response of the sample in response to each flow rate comprises: connecting a pressure transducer to the elongated tubular member; measuring a flow pressure of the sample using the pressure transducer in response to being flowed at each flow rate; and measuring a viscosity of the sample at each flow rate using the measured flow pressure at each flow rate.

A sixth aspect, combinable with any of the previous aspects, wherein the method further comprises, installing the elongated tubular member in a vertical orientation, and wherein measuring, at the wellbore drilling site and at each flow rate, a stress-strain response of the sample in response to each flow rate comprises: connecting a first pressure transducer and a second pressure transducer to the elongated tubular member at a respective first position and a second position on the elongated tubular member; measuring a first flow pressure of the sample using the first pressure transducer and a second flow pressure of the sample using the second pressure transducer in response to the sample being flowed at each flow rate; measuring a viscosity of the sample at each flow rate using either the measured first flow pressure or the measured second flow pressure at each flow rate; and measuring a density of the sample at each flow rate using the measured first flow pressure and the measured second flow pressure.

A seventh aspect, combinable with any of the previous aspects, wherein an inner diameter of the elongated tubular member is substantially equal to an inner diameter of a drill string being used in the wellbore drilling operation, wherein the drilling fluid is flowed through the drill string during the wellbore drilling operation.

An eighth aspect, combinable with any of the previous aspects, wherein the elongated tubular member comprises an inlet section and an outlet section, a length of each of the inlet section and the outlet section is at least ten times an inner diameter of the elongated tubular member.

A ninth aspect, combinable with any of the previous aspects, wherein the elongated tubular member is U-shaped.

A tenth aspect, combinable with any of the previous aspects, wherein flowing the sample through a tubular member at a plurality of different flow rates, the tubular member installed at the wellbore drilling site and measuring, at the wellbore drilling site and at each flow rate, a stress-strain response of the sample in response to each flow rate comprises, at each flow rate: flowing the sample through the tubular member for a duration sufficient to stabilize flow through the elongated tubular member; and measuring the stress-strain response of the sample after the duration has expired.

Other implementations of this aspect include corresponding systems, apparatus, and computer programs, configured to perform the actions of the methods, encoded on computer storage devices.

The details of one or more implementations of the subject matter described in this specification are set forth in the accompanying drawings and the description below. Other features, aspects, and advantages of the subject matter will become apparent from the description, the drawings, and the claims.

DESCRIPTION OF DRAWINGS

FIG. 2A is a schematic diagram that illustrates an example rheology measurement device according to a first implementation.

FIG. 2B is a schematic diagram that illustrates an example rheology measurement device according to a second implementation.

FIG. 2C is a schematic diagram that illustrates an example rheology measurement device according to a third implementation.

FIG. 2D is a schematic diagram that illustrates an example rheology measurement device according to a fourth implementation.

Like reference numbers and designations in the various drawings indicate like elements.

DETAILED DESCRIPTION

In some cases, the rheology data, for example, the stress-strain response data, of a drilling fluid can be measured in a laboratory using viscometers. Examples of the viscometers include the Fann Type 35 viscometers. In some cases, samples of the drilling fluid can be taken periodically, for example, every 6-8 hours, to the laboratory for measurement. The measured data can be analyzed to determine the rheological behavior of the fluid. However, the rheological behavior of the actual fluid used in the drilling operation can change much faster than a frequency at which samples are taken for laboratory measurement. For example, the temperature and the shear condition at a drilling site can change frequently. The composition of the fluid can also change due to loss of components to permeable formations and due to the addition of new fluid to compensate for the losses. These factors can have impact on the rheological behavior of the drilling fluid. Therefore, the rheological behavior of the drilling fluid analyzed in the laboratory can deviate from that of the actual fluid used in the drilling operation.

In some cases, the measured rheological data is used as input in simulations related to the drilling operations. Examples of these simulations include friction pressure or cuttings carrying capacity simulations. If the measured rheological data does not reflect the rheological behavior of the drilling fluid in real time, the simulation output can also provide erroneous results for the drilling operation.

In some cases, automated drilling fluid rheology measurement devices can be used to measure the rheology of the drilling fluid and feed the measurement data to simulation tools. Examples of these devices include BARALOGIX™ Density and Rheology Unit (DRU). However, similar to the viscometers used in laboratory rheology measurement, these devices can include complicated designs that are not suitable for drilling site operations. For example, these devices can use moving parts, such as a rotating bob inside a stationary cup, to hold the fluid. These devices are thus expensive to install and difficult to clean and maintain. These devices can also break down easily when operating under the rough environment of the drilling site.

This disclosure describes a rheology measurement system using an elongated tubular member installed at the drilling site to measure the rheological data at the drilling site. The rheology measurement device can provide a continuous measurement of the stress-strain data of the drilling fluid in real time before the fluid is fed to the mud pumps for circulation downhole. In some cases, the measurement data can be provided to a flow response computer system for analysis. The measurement data can be used to compare measurement data collected using the laboratory sampling method and adjust drilling operation simulations. FIGS. 1A-1B, 2A-2D, and 3-6 and associated descriptions provide additional details of these implementations.

Figure 1A:
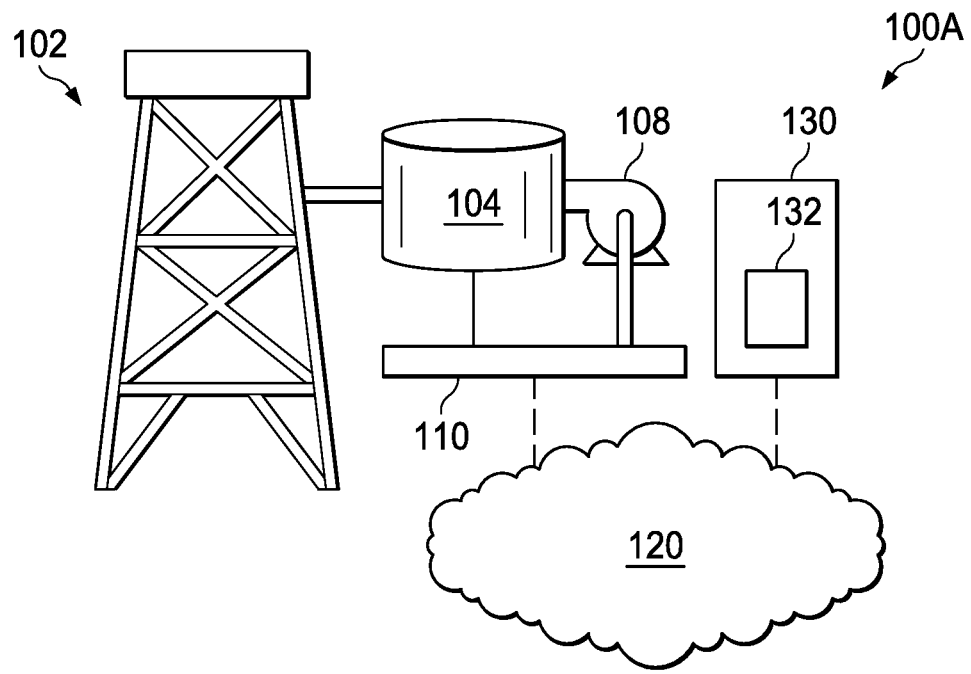
FIG. 1A is a schematic diagram that illustrates an example wellbore drilling system and an example drilling fluid analyzing system according to an implementation.
Figure 1B:
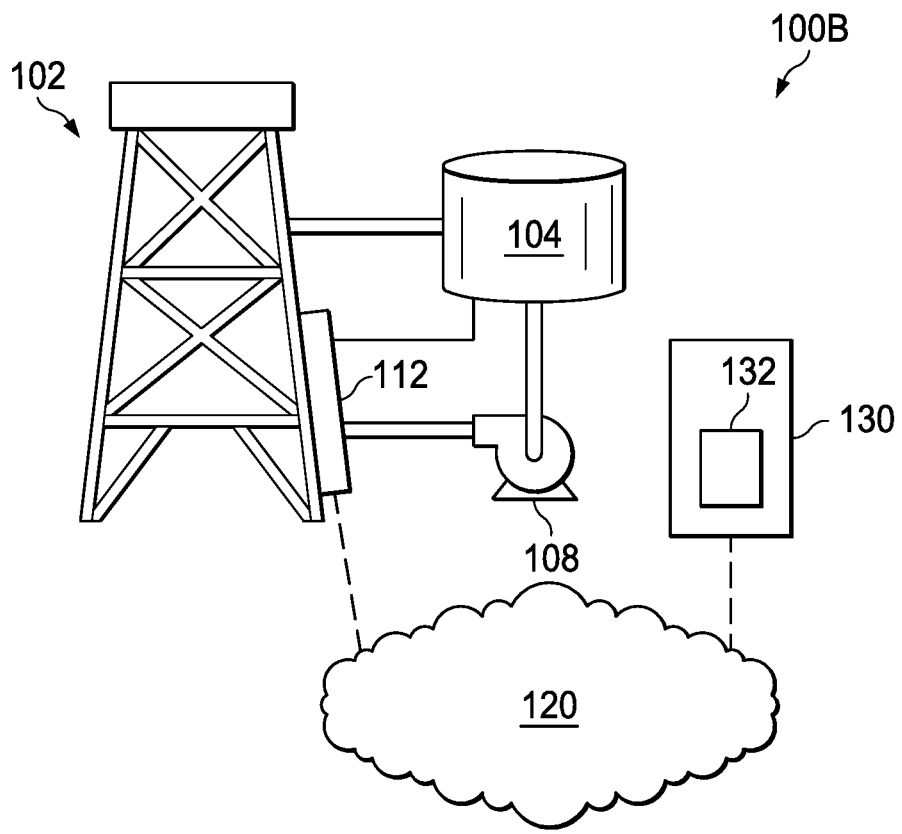
FIG. 1B is a schematic diagram that illustrates an example wellbore drilling system and an example drilling fluid analyzing system according to a different implementation.

FIGS. 1A and 1B are schematic diagrams that illustrate an example wellbore drilling system 102 and example drilling fluid analyzing systems 100A and 100B, respectively, according to respective implementations. The example wellbore drilling system 102 is installed at a wellbore drilling site. The example wellbore drilling system 102 includes a mud tank 104. The example drilling fluid analyzing system 100A includes a pump 108 connected with the mud tank 104 and a rheology measurement device 110. The example drilling fluid analyzing system 100A also includes a laboratory 130 that is communicatively coupled with the example drilling fluid analyzing system 100A over a network 120.

The example wellbore drilling system 102 can be implemented to extract one or more types of subterranean natural resources using boreholes. Examples of the subterranean natural resources can include hydrocarbon products such as natural gas or petroleum. In wellbore drilling situations that use a drilling rig, a wellbore drilling system circulates (or pumps) drilling fluid (for example, drilling mud) with one or more mud pumps. The example wellbore drilling system 102 moves drilling mud down into a wellbore, and drill collars which are connected to the drill sting. The fluid exits through ports (jets) in the drill bit, picking up cuttings and carrying the cuttings up the annulus of the wellbore. A mud pump takes suction from the mud tanks 104 and pumps mud out discharge piping, up the stand pipe, through rotary hoses, through Kelly or top drive unit, and into a central bore of the drill pipe, drill collars, and bit. Mud and cuttings return to the surface up annulus. At the surface, the mud and cuttings leave the wellbore through an outlet, and are sent to a cuttings removal system via mud return line. At the end of the return lines, mud and cutting are flowed onto a vibrating screen known in the art as a Shale Shaker. Finer solids can be removed by a sand trap. The mud can be treated with chemicals stored in a chemical tank and then provided into the mud tank 104, where the process is repeated.

The example wellbore drilling system 102 delivers large volumes of mud flow under pressure for drilling rig operations. The system 102 delivers the mud to the drill stem to flow down the string of drill pipe and out through the drill bit appended to the lower end of the drill stem. In addition to cooling the drill bit, the mud hydraulically washes away the face of the wellbore through a set of openings in the drill bit. The mud additionally washes away debris, rock chips, and cuttings, which are generated as the drill bit advances. The system 102 flows the mud in an annular space on the outside of the drill stem and on the interior of the open hole formed by the drilling process. In this manner, the system 102 flows the mud through the drill bit and out of the wellbore.

As shown in FIG. 1A, the pump 108 is connected to the mud tank 104. In some cases, the pump 108 can be implemented using a positive displacement pump, for example, a progressive cavity pump. The pump 108 can be driven by an Alternating Circuit (AC) electric motor. The pump 108 is configured to flow the samples of the drilling fluid from the mud tank 104 into the rheology measurement device 110. In some cases, the pump 108 can be configured to flow the samples at different flow rates. In some cases, the pump 108 can include, or be connected to, a variable frequency drive (VFD) that can be configured to control the rotation speed of the pump 108, thereby controlling the flow rate at different levels. In some cases, a programmable logic controller (PLC) system can be used to control the pump 108 to flow the samples at different flow rate.

The rheology measurement device 110 is configured to measure the rheological data of the sample drilling fluids flowed by the pump 108 from the mud tank 104. The sample drilling fluids are circulated back to the mud tank 104 after the measurement is taken. In some cases, the rheology measurement device 110 can include an elongated tubular member. The sample drilling fluid is flowed through the elongated tubular member. The rheology measurement device 110 can also include devices, for example, pressure transducers, that are configured to measure rheological data of the sample drilling fluid as the fluid flows through the elongated tubular member. FIGS. 2A-2D and associated descriptions include additional details of these implementations.

The laboratory 130 can be located at the drilling site close to the wellbore drilling system 102 or at a remote site. The laboratory 130 is communicatively coupled with the rheology measurement device 110 to receive the measurement data over the network 120. The network 120 can include a wireline network, a wireless network, or a combination thereof. For example, the network 120 can include a memory pipe, a hardware connection, or any internal or external communication paths between the components of a computer system. The network 120 can also include a wired or a wireless local area network (LAN), a cellular network, or a combination thereof.

The laboratory 130 can include a flow response computer system 132 that is configured to analyze the measurement data received from the rheology measurement device 110. For example, the rheology measurement device 110 can measure the pressures for different flow rate at which the sample drilling fluid flows through the elongated tubular member. The rheology measurement device 110 can send the pressure data to the flow response computer system 132 in the laboratory 130. The flow response computer system 132 can analyze the data and determine rheological data, for example, viscosity and density. FIGS. 2A-2D and associated descriptions include additional details of these implementations.

In operation, the pump 108 pumps sample drilling fluid from the mud tank 104 to the rheology measurement device 110. Because the samples are flown from the mud tank 104, the samples represent the drilling fluid that has either just exited the formation or is just about to enter the formation. Therefore, the sample is representative of the actual drilling fluid in real time. The pump 108 can be configured to pump the sample drilling fluid at different rate. These flow rates can reflect the range of the shear rates encountered when the drilling fluids are pumped into the drill string and circulated back up the annulus. For example, the pump 108 can be configured to pump the sample drilling fluid at a continuous circle of flow rates, starting at low rates of $8.3 \times 10^{-5}$ m$^3$/s or 5 l/min and stepwise, increasing to $1.6 \times 10^{-3}$ m$^3$/s or 100 l/min in 5 l/min increments. The rheology measurement device 110 measures a pressure for each flow rate at which the sample drilling fluid is flowed through the device 110. In some implementations, at each flow rate, the pump 108 can be configured to keep the flow rate constant for a configured time period, for example, for the flow to reach steady state. In some cases, the configured time period can be 30-60 seconds. Fresh water can be flushed into the rheology measurement device 110 after each cycle to clean the gelled fluid or solids and avoid buildup in the rheology measurement device 110.

In some implementations, the measurement data obtained by the rheology measurement device 110 can be sent to the laboratory 130, over the network 120, for analysis. In some cases, a reporting period can be configured and the measurement data can be reported during each reporting period. Example of the reporting period can be 5 minutes.

Alternatively or additionally, the measurement data can be analyzed on site. For example, for each flow rate, a user can read out the measured pressure data from the rheology measurement device 110, and calculate the viscosity based on the measured pressure data and the corresponding flow rate. A stress-strain curve can be determined based on the calculated viscosity. In some implementations, a calculation device, for example a computer, can be used to calculate the viscosity data and plot the stress-strain curve.

In some cases, the measurement data of the sample drilling fluid obtained at the drilling site can be compared with laboratory measurements. For example, a laboratory sample of the drilling fluid can be obtained from the wellbore drilling system 102. In some cases, the laboratory sample can be taken every 6-8 hours. Rheology measurements can be performed based on the laboratory samples, for example, in the laboratory 130. The stress-strain response data of the laboratory example, for example, flow pressure and viscosity, can be obtained and used as inputs to a mathematical model representing stress-strain behavior of the drilling fluid. The mathematical model can be used in friction pressure or cuttings carrying capacity simulations. In some cases, the measurement data obtained, based on the on-site drilling fluid taken in real time, can be used to compare with the measurement data based on the laboratory samples. The comparison can be used to adjust the mathematical model and reflect the effects of the changing temperature and shear conditions at the drilling site. In some cases, instead of, or in addition to, obtaining the absolute shear stress or shear rate readings, the changes of the stress-strain response data are obtained. These changes can indicate changes in the rheological behavior of the fluid in real time, relative to this initial laboratory test, and therefore can be used to adjust the simulations for the drilling operation. In some cases, adjustment can be made to the drilling operation based on the adjusted simulations using the real-time data. For example, additional fluid or chemicals can be added to the drilling fluid to maintain a rheological behavior.

In some cases, as shown in FIG. 1A, the rheology measurement device 110 can be installed in a horizontal orientation. For example, the rheology measurement device 110 can be attached to a structure on the surface. In one example, the rheology measurement device 110 can be installed along the side of the mud tank 104. Alternatively, the rheology measurement device 110 can be installed in a vertical orientation. FIG. 1B is a schematic diagram that illustrates an example drilling fluid drilling fluid analyzing system 100B, according to an implementation. As shown in FIG. 1B, the example drilling fluid analyzing system 100B includes a rheology measurement device 112 that is installed in a vertical orientation. The rheology measurement device 112 can be attached to a drilling rig in the wellbore drilling system 102. By including a rheology measurement device with vertical orientation, the example drilling fluid analyzing system 100B can measure additional parameters, for example density, of the fluid. FIG. 2D and associated descriptions include additional details of these implementations.

FIGS. 2A-2D are schematic diagrams that illustrate example rheology measurement devices 200A-200D, respectively, according to respective implementations. The example rheology measurement device 200A includes a pipe 202A and a pressure transducer 210 connected to the pipe 202A.

As shown in FIG. 2A, the pipe 202A is an elongated tubular member having a substantially or exactly circular cross-section. In some cases, the pipe 202A can be implemented using steel pipes, or any other materials that provide sufficient ruggedness for operations in a drilling site. In some cases, the inner diameters of the pipe 202A can be 0.5 inch or 1 inch. In some cases, the pipe 202A can be installed along the side of a mud tank, and the length of the pipe 202A can be similar to the length of a mud tank. For example, the length of the pipe 202A can be 25-30 feet. In some cases, the inner diameter of the pipe 202A can be substantially equal to an inner diameter of a drill string that is used to flow drilling fluid in a wellbore drilling operation.

The pipe 202A includes an inlet section 204 and an outlet section 206. In some cases, the length of both the inlet section 204 and the outlet section 206 is at least ten times of the inner diameter of the pipe 202A to eliminate end effects from differential pressure measurements.

The pressure transducer 210 can be implemented as one or more hardware, electronic circuit elements, software, or a combination thereof that can be configured to measure a flow pressure of the fluid flowing in the pipe 202A. In some cases, the pressure transducer 210 can be implemented using high-accuracy differential pressure transducer. Examples of the differential pressure transducers that can be used to implement the pressure transducer 210 include DELTA-BAR-FMD78 and OPTIBAR DP 7060C. In some cases, the pressure transducer 210 is connected to a middle section of the pipe 202, between the inlet section 204 and the outlet section 206 to prevent the end effects from measurements. In some cases, the pressure transducer 210 includes a transmitter that can be configured to transmit the measurement response to a flow response system for analysis.

In operation, the measurement fluid flows through the pipe 202A from the inlet section 204 to the outlet section 206. The pressure transducer 210 measure the flow pressure of the measurement fluid. A viscosity of the measurement fluid can be determined based on the flow pressure and the corresponding flow rate. In some cases, the measurement fluid can be flowed through the pipe 202A at different flow rates, a pressure corresponding to each flow rate can be measured by the pressure transducer 210, and a stress-strain response can be determined for each pair of pressure and flow rate. In some cases, the pipe 202A can be periodically cleaned by fresh water under high flow velocity through the pipe 202A. The fresh water can remove particles or solids that have settled at the pipe 202A.

Using the rheology measurement device as described herein provides one or more advantages. For example, comparing to conventional rheology measurement instruments such as Fann Type 35 Viscometer, the rheology measurement device described herein is simple to construct and easy to maintain. Furthermore, transducers and other components that are suitable for the explosive and hazardous environment on a drilling site can be selected to implement the rheology measurement.

In some cases, the pipe can be implemented as a U-shaped elongated tubular member. As shown in FIG. 2B, the example rheology measurement device 200B includes a U-shaped elongated pipe 202B and the pressure transducer 210. In some cases, using a U-Shaped pipe can simplify the installation of the example rheology measurement device 200B. For example, the inlet and the outlet of the pipe 202B can be placed close to each other, thereby increasing an available length of pipe while reducing a space occupied by the pipe. Such a U-shaped pipe also enables easy connection to the example rheology measurement device 200B with a holding tank that holds the measurement fluid.

In some cases, as shown in FIG. 2B, the two sections in the U-shape pipe can have the same inner diameters. Alternatively, the two sections can have different inner diameters. As shown in FIG. 2C, the example rheology measurement device 200C includes a pipe 202C and pressure transducers 212A and 212B. The pipe 202C includes a first section 208A and a second section 208B, each having a respective inner diameter different from that of the other. The pressure transducer 212A and the pressure transducer 212B is connected to the first section 208A and the second section 208B, respectively. Because the first section 208A and the second section 208B have different inner diameters, the flow pressures measured in these two sections can be different. In operation, the pressure transducers 208A-B can measure these different flow pressures. The viscosities corresponding these different flow pressure measurements can be calculated on site or by a flow response system. Measuring two different pressures for the same flow rate can increase an accuracy of the rheological data measured for the sample drilling fluid.

In some cases, as shown in FIG. 2D, the pipe of the rheology measurement device can be installed vertically. The example rheology measurement device 200D includes a pipe 202D that is installed vertically. The example rheology measurement device 200D also includes two pressure transducers: a pressure transducer 214A and a pressure transducer 214B. The pipe 202D can be attached to a substructure of the drilling rig.

The pressure transducers 214A and 214B can be positioned at different height to measure the density of the measurement fluid. For example, as shown in FIG. 2C, the pressure transducer 214A is positioned at a position that is H meter higher than the pressure transducer 214B. The H can be referred to as a hydrostatic pressure head. Therefore, the density of the measurement fluid can be calculated based on the differences of the flow pressures measured by the pressure transducers 214A and 214B and the value of the hydrostatic pressure head. The density can be calculated on site, by a calculating device, a person, or a combination thereof. The density can also be calculated by a fluid response computer system that are located in a laboratory.

As discussed previously, a fluid response computer system can receive the measured data from a rheology measurement device described herein and calculate rheological data based on the measured data. The flow response computer system can also use the rheological data as an input to a simulation program. The flow response computer system can execute the simulation program to simulate the performance of the drilling fluid in the wellbore drilling operation. In some cases, laboratory measurement of the drilling fluid can be obtained in a laboratory to compare with the on-site measurement obtained by the rheology measurement device 110.

Figure 3A:
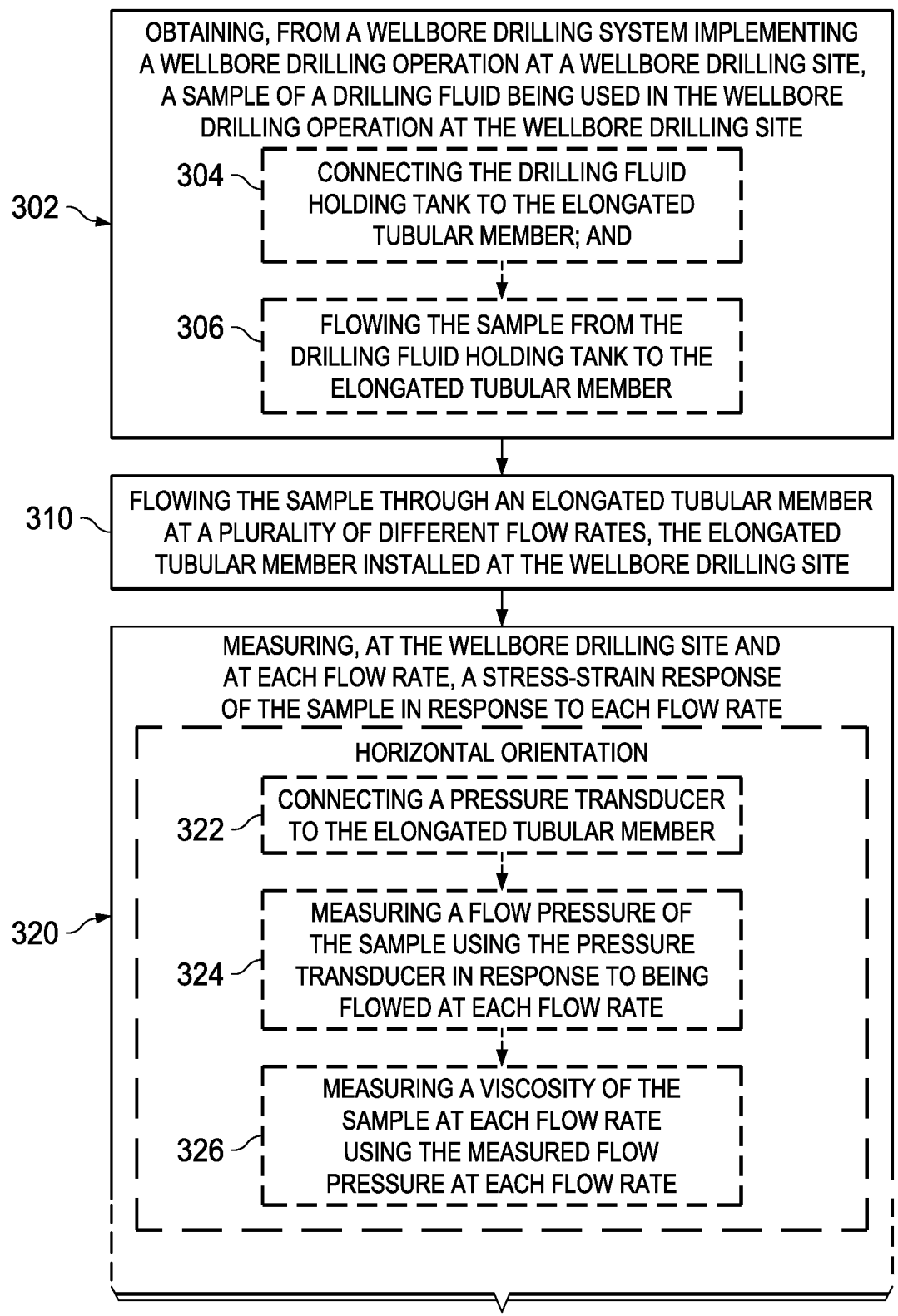
FIGS. 3A and 3B illustrate an example method for measuring stress-strain responses according to an implementation.
Figure 3B:
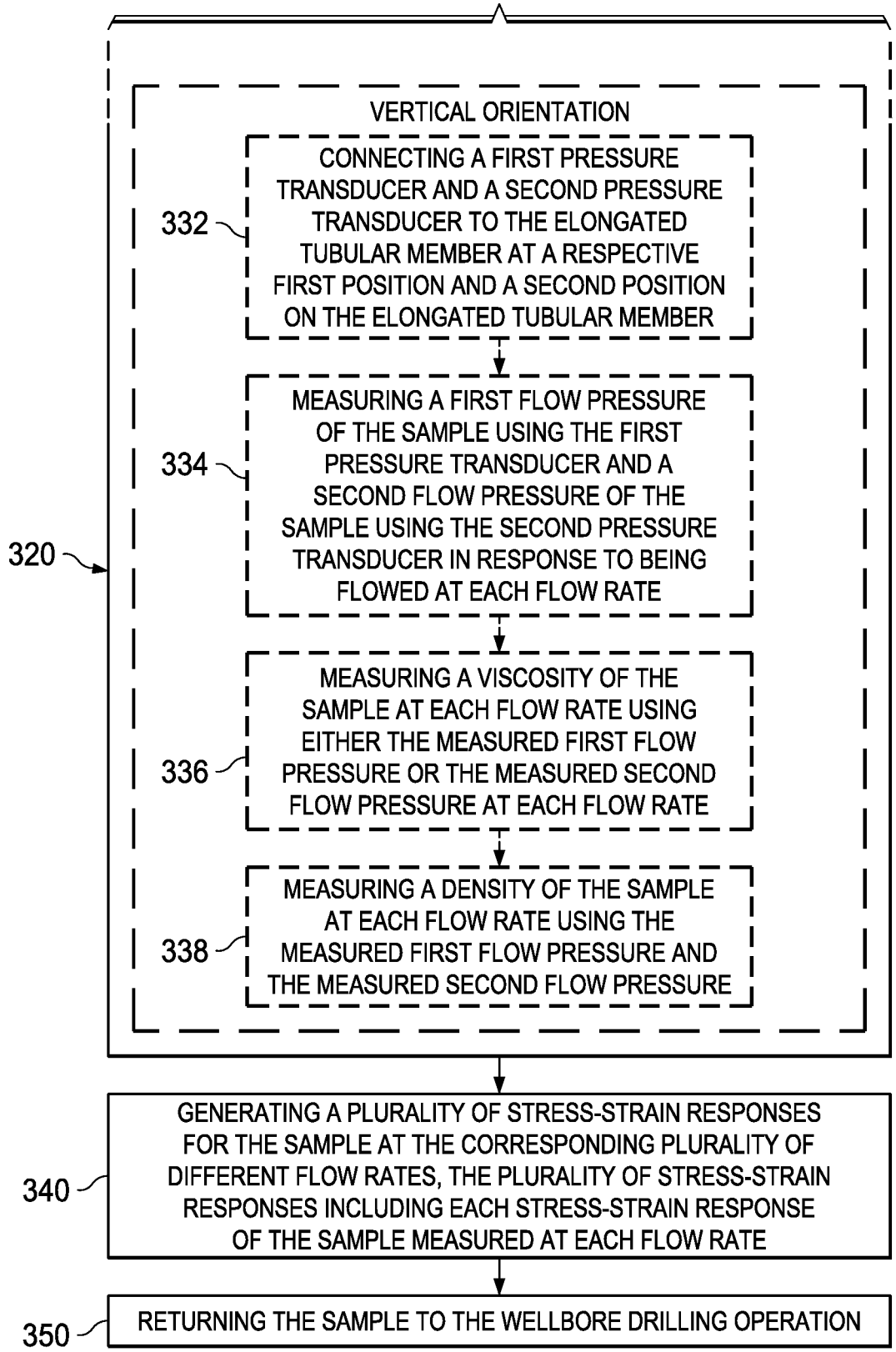

FIGS. 3A and 3B illustrate an example method 300 for measuring stress-strain responses according to an implementation. For clarity of presentation, the description that follows generally describes method 300 in the context of FIGS. 1A-1B, 2A-2D, and 4-6.

At 302, a sample of a drilling fluid is obtained from a wellbore drilling system, implementing a wellbore drilling operation, at a wellbore drilling site. The drilling fluid is used in the wellbore drilling operation at the wellbore drilling site. In some cases, the wellbore drilling operation includes a drilling fluid holding tank configured to receive the drilling fluid being used in the wellbore drilling operation. In these or other cases, the method 300 can optionally include steps 304-308 for obtaining the sample of the drilling fluid. At 304, the drilling fluid holding tank is connected with an elongated tubular member. At 306, the sample is flowed from the drilling fluid holding tank to the elongated tubular member.

At 310, the sample is flowed through the elongated tubular member at a plurality of different flow rates. The elongated tubular member is installed at the wellbore drilling site.

At 320, in response to each flow rate, a stress-strain response of the sample is measured at the wellbore drilling site at each flow rate. In some cases, the elongated tubular member can be installed in a horizontal orientation. In these or other cases, the method 300 can optionally include steps 322-326 for measuring the stress-strain response of the samples. At 322, a pressure transducer is connected to the elongated tubular member. At 324, a flow pressure of the sample is measured using the pressure transducer in response to being flowed at each flow rate. At 326, a viscosity of the sample at each flow rate is measured using the measured flow pressure at each flow rate.

In some cases, the elongated tubular member is installed in a vertical orientation. In these or other cases, the method 300 can optionally include steps 332-338 for measuring the stress-strain response of the samples. At 332, a first pressure transducer and a second pressure transducer are connected to the elongated tubular member at a respective first position and a second position on the elongated tubular member. At 334, a first flow pressure of the sample is measured using the first pressure transducer and a second flow pressure of the sample is measured using the second pressure transducer, in response to being flowed at each flow rate. At 336, a viscosity of the sample at each flow rate is measured using either the measured first flow pressure or the measured second flow pressure, at each flow rate. At 338, a density of the sample at each flow rate is measured using the measured first flow pressure and the measured second flow pressure.

At 340, a plurality of stress-strain responses for the sample at the corresponding plurality of different flow rates are generated. The plurality of stress-strain responses includes each stress-strain response of the sample measured at each flow rate.

At 350, the sample is returned to the wellbore drilling operation.

Figure 4:
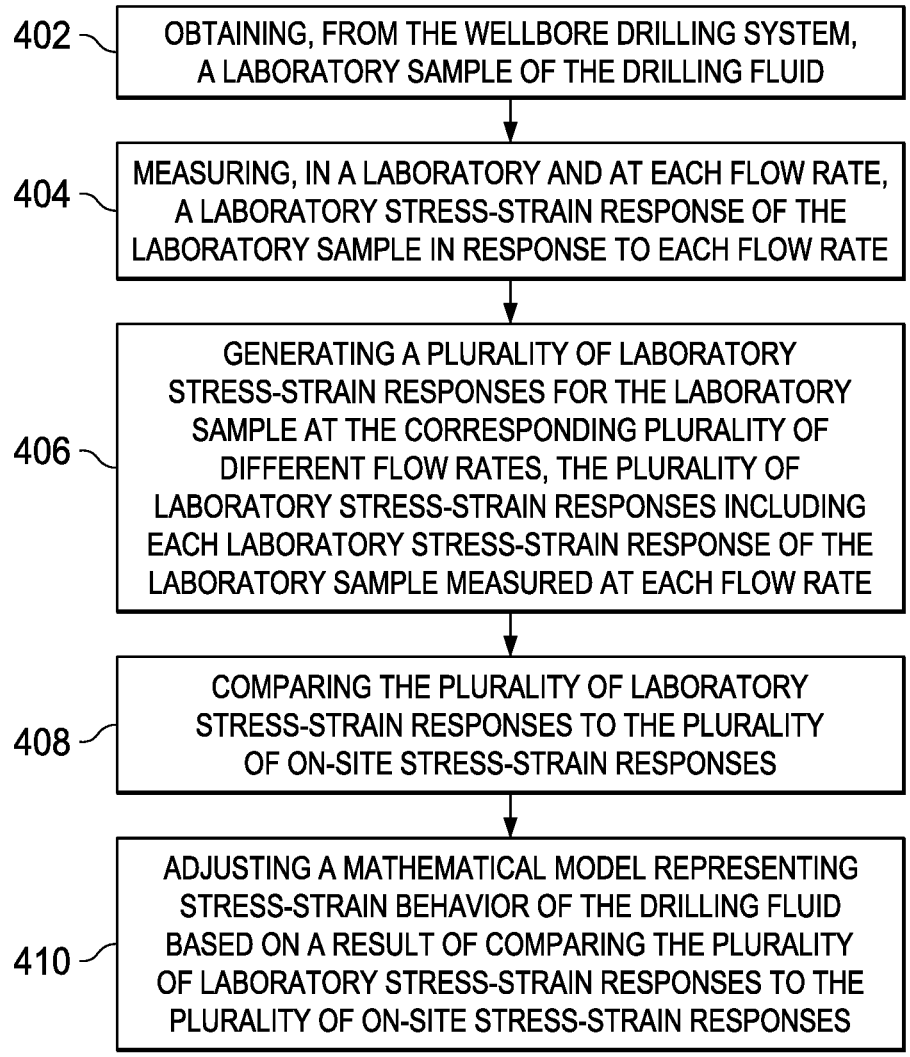
FIG. 4 illustrates an example method for comparing measured stress-strain responses with laboratory measurements according to an implementation.

In some cases, the stress-strain responses measured from the on-site samples can be used to compare with measurement based on a laboratory sample. FIG. 4 illustrates an example method 400 for comparing measured stress-strain responses with laboratory measurements according to an implementation. For clarity of presentation, the description that follows generally describes method 400 in the context of FIGS. 1A-1B, 2A-2D, 3A-3B, and 5-6.

At 402, a laboratory sample of the drilling fluid is obtained from the wellbore drilling system. At 404, a laboratory stress-strain response of the laboratory sample is measured in response to each flow rate in a laboratory and at each flow rate. At 406, a plurality of laboratory stress-strain responses for the laboratory sample at the corresponding plurality of different flow rates is generated. The plurality of laboratory stress-strain responses includes each laboratory stress-strain response of the laboratory sample measured at each flow rate. At 408, the plurality of laboratory stress-strain responses is compared to the plurality of on-site stress-strain responses. At 410, a mathematical model representing stress-strain behavior of the drilling fluid is adjusted based on a result of comparing the plurality of laboratory stress-strain responses to the plurality of on-site stress-strain responses.

Figure 5:
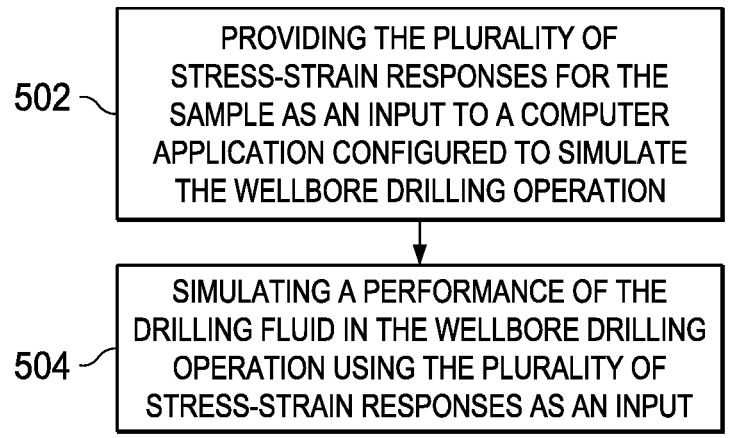
FIG. 5 illustrates an example method for simulating drilling fluid performance according to an implementation.

In some cases, the stress-strain responses measured from the on-site samples can be used to simulate drilling fluid performance. FIG. 5 illustrates an example method 500 for simulating drilling fluid performance according to an implementation. For clarity of presentation, the description that follows generally describes method 500 in the context of FIGS. 1A-1B, 2A-2D, 3A-3B, 4, and 6.

At 502, the plurality of stress-strain responses for the sample are provided as an input to a computer application configured to simulate the wellbore drilling operation. At 504, a performance of the drilling fluid in the wellbore drilling operation is simulated using the plurality of stress-strain responses as an input. In some cases, at least one of a friction pressure of the drilling fluid or cutting carrying capacity of the drilling fluid in the wellbore drilling operation is simulated.

Figure 6:
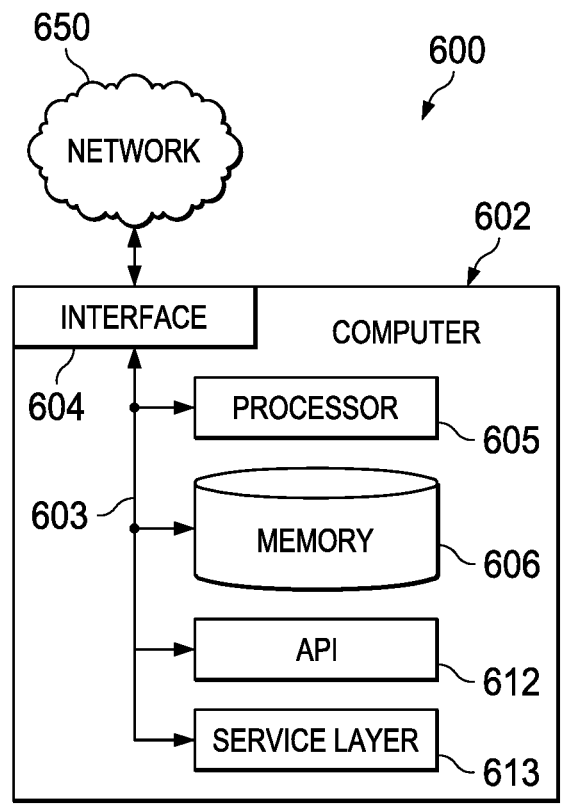
FIG. 6 is a high-level architecture block diagram of a flow response analysis system according to an implementation.

FIG. 6 is a high-level architecture block diagram of a flow response analysis system 600 according to an implementation. At a high level, the illustrated system 600 includes a flow response computer system 602 that is communicably coupled with a network 650. The described illustration is only one possible implementation of the described subject matter and is not intended to limit the disclosure to the single described implementation. Those of ordinary skill in the art will appreciate the fact that the described components can be connected, combined, or used in alternative ways consistent with this disclosure.

The network 650 facilitates communications between the components of the system 600 with other components. For example, the flow response computer system 602 can be connected to a flow measurement system over the network 650 to receive flow response measurement data. The flow response computer system 602 can receive requests over network 650 from a client application and respond to the received requests by processing the requests in an appropriate software application. In addition, requests can also be sent to the flow response computer system 602 from internal users (for example, from a command console or by another appropriate access method), external or third parties, other automated applications, as well as any other appropriate entities, individuals, systems, or computers.

The flow response computer system 602 includes a computer configured to analyze flow response data. In some cases, the algorithm of the relative permeability data correction process can be implemented in an executable computing code, for example C/C++ executable codes, an application program, for example, EXCEL, or another other computer programs.

The flow response computer system 602 can comprise a computer that includes an input device, such as a keypad, keyboard, touch screen, microphone, speech recognition device, other device that can accept user information, or an output device that conveys information associated with the operation of the computer, including digital data, visual or audio information, or a GUI.

Each of the components of the flow response computer system 602 can communicate using a system bus 603. In some implementations, any or all the components of the flow response computer system 602, both hardware or software, can interface with each other or the interface 604 over the system bus 603 using an application programming interface (API) 612 or a service layer 613.

The flow response computer system 602 includes an interface 604. Although illustrated as a single interface 604 in FIG. 6, two or more interfaces 604 can be used according to particular needs, desires, or particular implementations of the flow response computer system 602. The interface 604 is used by the flow response computer system 602 for communicating with other systems in a distributed environment—including within the system 500—connected to the network 630 (whether illustrated or not).

The flow response computer system 602 includes a processor 605. Although illustrated as a single processor 605 in FIG. 6, two or more processors can be used according to particular needs, desires, or particular implementations of the flow response computer system 602 or the system 600. Generally, the processor 605 executes instructions and manipulates data to perform the operations of the flow response computer system 602. Specifically, the processor 605 executes the functionality required for correcting relative permeability data. In some cases, the processor 605 can include a data processing apparatus.

The flow response computer system 602 also includes a memory 606 that holds data for the flow response computer system 602 or other components of the system 600. Although illustrated as a single memory 606 in FIG. 6, two or more memories can be used according to particular needs, desires, or particular implementations of the flow response computer system 602 or the system 600. While memory 606 is illustrated as an integral component of the flow response computer system 602, in alternative implementations, memory 606 can be external to the flow response computer system 602 or the system 600.

Implementations of the subject matter and the operations described in this specification can be implemented in digital electronic circuitry, or in computer software, firmware, or hardware, including the structures disclosed in this specification and their structural equivalents, or in combinations of one or more of them. Embodiments of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially-generated propagated signal, e.g., a machine-generated electrical, optical, or electromagnetic signal, which is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially-generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations of the foregoing The apparatus can include special purpose logic circuitry, e.g., an FPGA (field programmable gate array) or an ASIC (application-specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

This specification is presented to enable any person skilled in the art to make and use the disclosed subject matter, and is provided in the context of one or more particular implementations. Various modifications to the disclosed implementations will be readily apparent to those skilled in the art, and the general principles defined herein can be applied to other implementations and applications without departing from scope of the disclosure. Thus, the present disclosure is not intended to be limited to the described or illustrated implementations, but is to be accorded the widest scope consistent with the principles and features disclosed herein.

Accordingly, the above description of example implementations does not define or constrain this disclosure. Other changes, substitutions, and alterations are also possible without departing from the spirit and scope of this disclosure.

What is claimed is:

1. A method comprising:
obtaining, from a wellbore drilling system implementing a wellbore drilling operation at a wellbore drilling site, a sample of a drilling fluid being used in the wellbore drilling operation at the wellbore drilling site;
flowing the sample through an elongated tubular member at a plurality of different flow rates, the elongated tubular member installed at the wellbore drilling site, wherein the elongated tubular member comprises a first section and a second section, both the first section and the second section are straight, the first section connects to the second section to form a "U" shape, the first section has a first inner diameter, the second section has a second inner diameter, the first inner diameter is larger than the second inner diameter, and wherein the drilling fluid is flowed through a drill string beneath a surface of the wellbore drilling site during a wellbore drilling operation, the elongated tubular member is installed above the surface of the wellbore drilling site and separated from the drill string, and at least one of the first inner diameter or the second inner diameter is equal to an inner diameter of the drill string;
measuring, at the wellbore drilling site and at each flow rate, a stress-strain response of the sample in response to each flow rate;
generating a plurality of stress-strain responses for the sample at the corresponding plurality of different flow rates, the plurality of stress-strain responses including each stress-strain response of the sample measured at each flow rate; and
returning the sample to the wellbore drilling operation.

2. The method of claim 1, wherein the sample is an on-site sample, the plurality of stress-strain responses is a plurality of on-site stress-strain responses, and wherein the method further comprises:
obtaining, from the wellbore drilling system, a laboratory sample of the drilling fluid;
measuring, in a laboratory and at each flow rate, a laboratory stress-strain response of the laboratory sample in response to each flow rate;
generating a plurality of laboratory stress-strain responses for the laboratory sample at the corresponding plurality of different flow rates, the plurality of laboratory stress-strain responses including each laboratory stress-strain response of the laboratory sample measured at each flow rate;
comparing the plurality of laboratory stress-strain responses to the plurality of on-site stress-strain responses; and
adjusting a mathematical model representing stress-strain behavior of the drilling fluid based on a result of comparing the plurality of laboratory stress-strain responses to the plurality of on-site stress-strain responses.

3. The method of claim 1, further comprising:
providing the plurality of stress-strain responses for the sample as an input to a computer application configured to simulate the wellbore drilling operation; and
simulating a performance of the drilling fluid in the wellbore drilling operation using the plurality of stress-strain responses as an input.

4. The method of claim 3, wherein simulating the performance of the drilling fluid in the wellbore drilling operation comprises simulating at least one of a friction pressure of the drilling fluid or cutting carrying capacity of the drilling fluid in the wellbore drilling operation.

5. The method of claim 1, wherein the wellbore drilling operation comprises a drilling fluid holding tank configured to receive the drilling fluid being used in the wellbore drilling operation, and wherein obtaining the sample of the drilling fluid comprises:
connecting the drilling fluid holding tank to the elongated tubular member; and
flowing the sample from the drilling fluid holding tank to the elongated tubular member.

6. The method of claim 1, further comprising installing the elongated tubular member in a horizontal orientation, and wherein measuring, at the wellbore drilling site and at each flow rate, a stress-strain response of the sample in response to each flow rate comprises:
connecting a pressure transducer to the elongated tubular member;
measuring a flow pressure of the sample using the pressure transducer in response to being flowed at each flow rate; and
measuring a viscosity of the sample at each flow rate using the measured flow pressure at each flow rate.

7. The method of claim 1, further comprising installing the elongated tubular member in a vertical orientation, and wherein measuring, at the wellbore drilling site and at each flow rate, a stress-strain response of the sample in response to each flow rate comprises:
connecting a first pressure transducer and a second pressure transducer to the elongated tubular member at a respective first position and a second position on the elongated tubular member;
measuring a first flow pressure of the sample using the first pressure transducer and a second flow pressure of the sample using the second pressure transducer in response to the sample being flowed at each flow rate;
measuring a viscosity of the sample at each flow rate using either the measured first flow pressure or the measured second flow pressure at each flow rate; and
measuring a density of the sample at each flow rate using the measured first flow pressure and the measured second flow pressure.

8. The method of claim 1, wherein the elongated tubular member comprises an inlet section and an outlet section, a length of each of the inlet section and the outlet section is at least ten times an inner diameter of the elongated tubular member.

9. The method of claim 1, wherein flowing the sample through a tubular member at a plurality of different flow rates, the tubular member installed at the wellbore drilling site and measuring, at the wellbore drilling site and at each flow rate, a stress-strain response of the sample in response to each flow rate comprises, at each flow rate:
flowing the sample through the tubular member for a duration sufficient to stabilize flow through the elongated tubular member; and
measuring the stress-strain response of the sample after the duration has expired.

10. A drilling fluid rheology analysis system comprising:
an elongated tubular member installed at a wellbore drilling site, the elongated tubular member attached to a drilling fluid tank of a wellbore drilling system installed at the wellbore drilling site, the drilling fluid tank configured to receive a drilling fluid being used in a wellbore drilling operation at the wellbore drilling site, the elongated tubular member configured to receive a sample of the drilling fluid being used in the wellbore drilling operation, wherein the elongated tubular member comprises a first section and a second section, each of the first section and the second section is straight, the first section connects to the second section to form a "U" shape, the first section has a first inner diameter, the second section has a second inner diameter, the first inner diameter is larger than the second inner diameter, and wherein the drilling fluid is flowed through a drill string beneath a surface of the wellbore drilling site during the wellbore drilling operation, the elongated tubular member is installed above the surface of the wellbore drilling site and separated from the drill string, and at least one of the first inner diameter or the second inner diameter is equal to an inner diameter of the drill string;
a pump connected to the elongated tubular member, the pump configured to flow the sample through the elongated tubular member at a plurality of different flow rates;
a flow measurement system connected to the elongated tubular member, the flow measurement system configured to measure, at each flow rate, a viscosity of the sample in response to each flow rate; and
a flow response computer system configured to perform operations comprising:
receiving, for each flow rate, a viscosity of the sample in response to each flow rate, and
generating a plurality of viscosities for the sample at the corresponding plurality of different flow rates, the plurality of viscosities including each stress-strain response of the sample measured at each flow rate.

11. The system of claim 10, wherein the sample is an on-site sample, the plurality of viscosities is a plurality of on-site viscosities, and wherein the flow response computer system is configured to perform operations comprising:
receiving a plurality of laboratory viscosities for a laboratory sample obtained from the drilling fluid, the plurality of laboratory viscosities determined at the corresponding plurality of different flow rates, the plurality of laboratory viscosities including each laboratory viscosity of the laboratory sample measured at each flow rate;
comparing the plurality of laboratory viscosities to the plurality of on-site viscosities; and
adjusting a mathematical model representing viscosity behavior of the drilling fluid based on a result of comparing the plurality of laboratory viscosities to the plurality of on-site viscosities.

12. The system of claim 10, wherein the flow response computer system is configured to perform operations comprising:
providing the plurality of viscosities for the sample as an input to a computer application configured to simulate the wellbore drilling operation; and
simulating a performance of the drilling fluid in the wellbore drilling operation using the plurality of viscosities as an input.

13. The system of claim 10, wherein the elongated tubular member is horizontal, and wherein the flow measurement system connected to the elongated tubular member comprises a pressure transducer connected to the elongated tubular member, the pressure transducer configured to measure a flow pressure of the sample at each flow rate.

14. The system of claim 10, wherein the elongated tubular member is vertical, and wherein the flow measurement system connected to the elongated tubular member comprises a first pressure transducer and a second pressure transducer connected to the elongated tubular member at a respective first position and a second position on the elongated tubular member, the first pressure transducer and the second pressure transducer configured to measure a first flow pressure and a second flow pressures, respective, of the sample at each flow rate.

15. The system of claim 10, wherein the elongated tubular member comprises an inlet section and an outlet section, a length of each of the inlet section and the outlet section is at least ten times an inner diameter of the elongated tubular member.

16. The system of claim 10, wherein the pump is configured to flow the sample through the elongated tubular member for a duration sufficient to stabilize flow through the elongated tubular member, and wherein the flow measurement system is configured to measure, at each flow rate, a viscosity of the sample in response to each flow rate after the duration has expired.

* * * * *